United States Patent [19]

Lang

[11] 4,125,770
[45] Nov. 14, 1978

[54] DIAMOND IDENTIFICATION

[76] Inventor: Andrew R. Lang, 1B Elton Rd., Bristol BS8 1SJ, England

[21] Appl. No.: 811,764

[22] Filed: Jun. 30, 1977

Related U.S. Application Data

[63] Continuation of Ser. No. 645,347, Dec. 30, 1975, abandoned.

[30] Foreign Application Priority Data

Jan. 3, 1975 [GB] United Kingdom .................. 328/75

[51] Int. Cl.$^2$ ..................... G01N 21/00; G01N 23/20; G21K 1/00
[52] U.S. Cl. .................................. 250/272; 250/273; 250/275; 356/30
[58] Field of Search ............... 250/272, 274, 273, 275, 250/320, 321, 323; 356/30

[56] References Cited

U.S. PATENT DOCUMENTS

| | | | |
|---|---|---|---|
| 1,799,604 | 4/1931 | Read | 356/30 |
| 3,792,269 | 2/1974 | Grienauer | 250/272 |
| 3,947,120 | 3/1976 | Bar-Issac et al. | 356/30 |

OTHER PUBLICATIONS

Kohn, J. A., "Diamond, Natural and Synthetic: X-Ray Studies," *Encyclopedia of X-Rays and Gamma Rays,* Edited by George L. Clark, Reinhold Publishing Co., New York, 1963, p. 231.

Lange, A. R., "Topography, X-Ray Diffraction," *Encyclopedia of X-Rays and Gamma Rays,* Edited by George L. Clark, Reinhold Publishing Co., New York, 1963, p. 231.

Spencer et al., "Camera for X-Ray Diffraction Topography," *Review of Scientific Instruments,* vol. 34, No. 12, Dec. 1963, pp. 1420–1422.

*Primary Examiner*—Alfred E. Smith
*Assistant Examiner*—T. N. Grigsby
*Attorney, Agent, or Firm*—Cushman, Darby & Cushman

[57] ABSTRACT

A method of determining whether a diamond is the same as or different to a known diamond characterized by the steps of producing one or more records of internal defects of the diamond using X-ray topography and comparing the record or records so produced with a similar record or records produced from the known diamond.

17 Claims, 4 Drawing Figures

DIAMOND IDENTIFICATION

This is a continuation of application Ser. No. 645,347 filed Dec. 30, 1975 and now abandoned, the entire specification of which is hereby incorporated by reference.

This invention relates to the identification of diamonds, particularly diamonds of gem stone quality.

Diamonds of gem stone quality have of course been for many years of great value both for decorative and for investment purposes. The value of such diamonds has continued to increase, and this very increase in value had raised further problems for the police authorities and insurance companies. When a gem diamond is lost or is stolen, it can be difficult for the police authorities to identify a recovered diamond as being that which was stolen or lost especially since the nature of the diamond can be superficially changed by such techniques as re-polishing, re-cutting and irradiation.

The identification of a recovered diamond has in the past been performed by assembling a "finger print" of the easily recognised features of the diamond. Such features include the carat weight, cut, clarity and colour of the diamond; others are the results of various physical tests performed on the diamond. The latter features include the measurement of surface irregularities using e.g. the Nomarski differential interference contrast, or techniques measuring bulk average properties e.g. fluorescence, magnetic, optical absorption and electron spin resonance measurements. However, although such a finger print of a diamond might be constant enough to enable the authorities to identify a particular diamond when it is recovered, this can only be done if the nature of the diamond has not been changed as mentioned above. Further, this finger printing technique can in general only be performed on cut diamonds; it is not suitable for rough diamonds. However, the security arrangements in diamond mines and in diamond cutting establishments do require that a check can be made at all times on the rough diamonds and then the partially cut and fully cut diamonds passing through the mine or cutting establishment. There is at present no technique available for identifying a particular cut diamond from the rough stone from which it has been cut; clearly there is a need for such a method.

It has now been found that the application of topography can provide a finger print of a diamond, both in the rough as well as the cut state, which finger print is not changed if the diamond is subjected to re-polishing, recutting an/or mild irradiation. The finger print is only changed if the characteristic crystalline nature of the diamond is profoundly changed by converting it, for example, to amorphous carbon. Topography is a technique which depicts point-by-point throughout its whole volume certain properties of a specimen. Thus topographical studies are of particular value whenever the inhomogeneity of the specimen is of interest (see e.g. Lang, "Modern Diffraction and Imaging Techniques in Material Science," North-Holland Publishing Co., Amsterdam-London, 407 (1970)).

Figure 1:
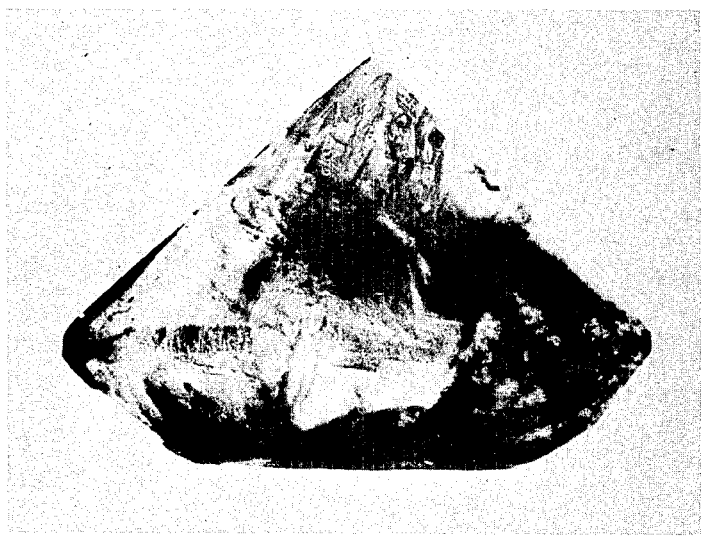
FIG. 1 is a projection topograph of a one carat brilliant diamond.

The method of the invention involves determining whether a diamond is the same as or different to a known diamond by producing one or more records of internal defects of the diamond using X-ray topography and comparing the record or records so produced with a similar record or records produced from the known diamond. The record or records are preferably produced using X-ray diffraction at the Bragg angle. By the term "Bragg angle" is meant the angle which satisfies the equation known as Bragg's Law:

$$2d_{hkl} \sin \theta = n\lambda$$

In this equation, $d_{hkl}$ is the interplanar spacing of those crystal lattice planes whose orientation in the crystal lattice is denoted by the index hkl, the angle $\theta$ is the angle made by the beam of X-rays with the above-mentioned planes, $n$ is an integer and $\lambda$ is the wavelength of the X-rays concerned. X-ray diffraction radiographs (also known as X-ray diffraction topographs) taken at the Bragg angle show characteristic patterns, which are of such a nature that it is unlikely that more than one diamond will possess exactly the same finger print, particularly if a series of X-ray diffraction radiographs are taken in the various planes but still using the Bragg reflection angle. The record or records may be X-ray diffraction or absorption topographs, but are preferably diffraction topographs. It is to be understood that the expression "using X-ray diffraction at the Bragg Angle" is employed herein in the general sense. If the specimen contains some regions of the crystal which are significantly misoriented with respect to other regions in the crystal then, when the wavelengths contained in the X-ray beam incident upon the crystal are restricted to a sufficiently narrow range, and there is a sufficiently small angular divergence of the X-ray beam incident upon the specimen, some crystal regions may satisfy Bragg's Law whereas others may in effect fail to do so, at a given angular setting of the crystal with respect to the mean orientation of the incident X-ray beam. Such a misorientation in the specimen can be recorded, and may in fact be included as comprising part of the X-ray topographic record of internal defects in the diamond. The sensitivity of contrast, nature of contrast (i.e. excess or deficiency of diffracted intensity) and the range of contrast with which these misorientations (and also lesser mis-orientations such as are associated with individaul crystal lattice dislocations) are recorded depend upon the degree of collimation and wavelength spread of the X-rays incident upon the specimen. Thus the contrast characteristics of the X-ray topographs will in general depend upon whether the X-radiation incident upon the specimen is collimated by slits, or is collimated and/or monochromatized by prior Bragg reflection by a so called "monochromator" crystal, and also upon whether the origin of the radiation is a conventional X-ray generator or is a synchrotron source. It is to be understood that such practical variations and subtleties are included within the terms "using X-ray diffraction at the Bragg angle" and "satisfying Bragg's Law," as used herein.

In the method of the invention there can be used the Bragg reflection from one, or more than one, crystal lattice plane differing in orientation and/or interplanar spacing by means of projection and/or section topography according to a predetermined routine designed to maximise the information content regarding the internal distinguishing features of the crystal. The use of this X-ray topographic technique makes it possible to identify crystal lattice imperfections e.g. crystal lattice dislocations in the diamond, growth bands, stacking faults and twinning.

As will be seen from the Bragg's Law equation, if the X-radiation is monochromatic (or nearly so) then the crystal must be set at such an angle with respect to the range of directions of rays contained within the incident X-ray beam that the Bragg's Law equation is satisfied for at least one crystal lattice plane (hkl). In this case, the X-ray topographs will be recorded serially. On the other hand, if the X-radiation is not monochromatic, such as the so-called "white radiation" emitted by an X-ray tube, or the X-rays produced by a synchrotron, then, at each angular setting of the crystal with respect to the incident beam, a group of Bragg reflections, each arising from a differently oriented crystal lattice plane, may be simultaneously recorded as in the technique described by Guinier and Tennevin, Acta Crystallographica, 1949, 2, 133–8. It is a matter of choice, depending much upon the characteristics of the X-ray source available, whether Bragg reflections are recorded serially (making use of X-rays of a given wavelength) or simultaneously in groups as in the technique of Guinier and Tennevin cited above. If the latter technique is used, then it would be advantageous to record groups of reflections when a symmetry axis is oriented parallel to the axis of the incident X-ray beam. For Example, groups of reflections could be recorded with, for each group, one of the three cubic symmetry axes oriented parallel to the beam.

As indicated above a series of diffraction radiographs using crystallographically equivalent reflections can be taken. The simplest routine, when using monochromatic radiation, is to select the three cube planes in which four radiographs are taken in each plane; between the taking of each radiograph, the crystal is rotated 90° round the perpendicular to the plane to give an overall picture of the stone.

The radiograph can be registered in permanent or semi-permanent form by the usual techniques, e.g. by X-ray polaroid techniques, X-ray sensitive photographic emulsions, xerography and electronic techniques; such electronic techniques include electronic image intensifiers (with or without television apparatus added thereto) and position-sensitive gas-filled or solid-state X-ray photon detectors (used singly, or multiply in an array). The records may, for example, be in the form of magnetic tapes. The source of the X-rays (which should be collimated) can be either from a conventional X-ray tube or from a synchrotron, the synchrotron being a source of highly collimated and highly intense X-rays.

It is possible to distinguish between synthetic and natural diamonds by this topographic technique, in general because the synthetic diamonds currently available possess types of inclusion, due, for example, to metallic impurities, which are not present in natural diamonds.

Some diamonds e.g. rough diamonds, particularly those from an alluvial source have surface damage and it is desirable to remove as much of the surface damage as possible prior to producing the X-ray topograph record or records of the diamond. Removal of surface damage enables the internal distinguishing features of the diamond to be revealed with improved clarity and contrast in the X-ray topographs. Surface damage may be removed by etching using for example a gas at controlled temperatures and pressures, reactive gases in the presence of electric currents, agitated liquids and high velocity ions and atoms.

Where a rough diamond has a coating thereon, the X-ray topograph or topographs can indicate whether the stone is worth the expense and effort of opening it.

It is believed that the insurance companies and police authorities will build up an index of X-ray topographs of known diamonds and such an index forms part of my invention. For example the index may comprise an abstract, summary or codification descriptive of the configurations of one or more types of internal defects, such as stacking faults, twins, slip bands and small-angle grain boundaries (mis-orientations) and, especially, lattice dislocations, growth horizons and strain fields associated with submicroscopic inclusions or precipitates, as recorded by X-ray topography.

Figure 2:
FIG. 2 is a section topograph of the diamond.

The accompanying radiographs (FIGS. 1 and 2) show X-ray diffraction pictures of a one carat brilliant diamond. FIG. 1 is a projection topograph (Lang, Acta Crystallographica, 1959, 12, 249–350), while FIG. 2, which is roughly elliptical in shape, is an X-ray section topograph (this technique is discussed by Lang, Acta Metallurgica, 1957, 5, 358–364) cutting through the brilliant diamond roughly parallel to its widest section parallel to the table, i.e. a section parallel to the girdle. The section topograph shows very sharp detail and hence a high degree of uniqueness, but it represents just one cut through the crystal. The projection topograph shows a reflection of the whole volume of the crystal and so is somewhat less sharp. This particular diamond is rather pathological from the crystal growth point of view (but, apparently, having an internal structure not very uncommon). Hence it was not an easy subject for finger printing since it contained so much imperfection. However, it is felt confident that the pictures, plus possibly a few more of the same stone, would constitute a unique and unambiguous finger print, unalterable by any method that would not also ruin the stone itself.

Figure 3:
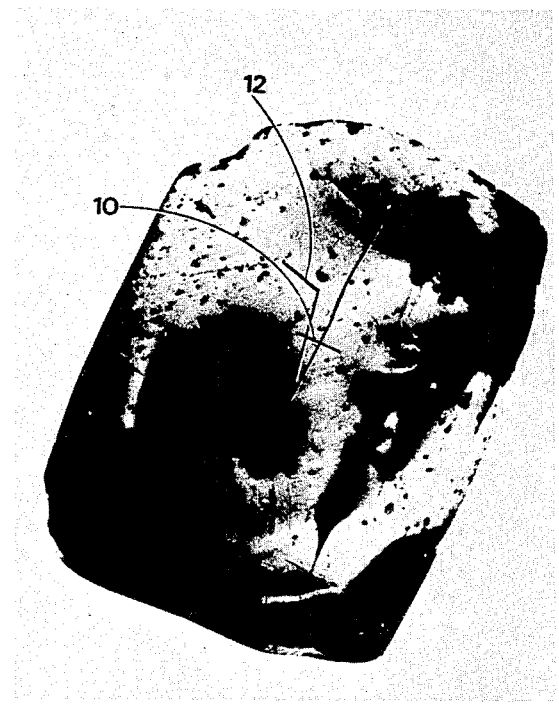
FIG. 3 is a topograph of an uncut diamond.
Figure 4:
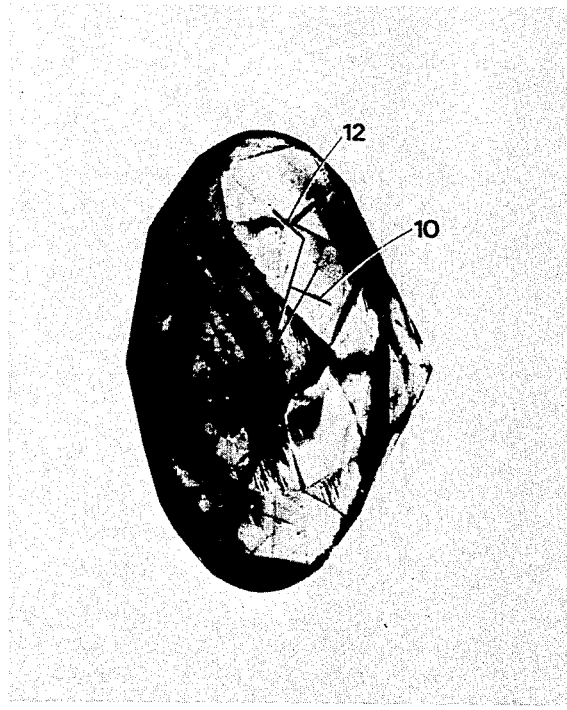
FIG. 4 is a topograph of the diamond of FIG. 3 after cutting.

In an example of the invention, X-ray diffraction topographs of three rough diamonds, all of gem stone quality with no visible flaws nor any microscopically visible identifying characteristics of any sort, were taken. In order to obtain a reasonably complete diffraction topographic record of the rough stones for "finger printing" purposes, and yet keep the number of topographs to be taken to a minimum, it was decided to use the reflections of the form of lowest multiplicity, namely the cube {100}, and to obtain projection topographs using each independent plane of this form, of which there are three. The lowest-order reflection from this form allowed by the symmetry of the space-group to which diamond belongs (namely $O_h^7$) is of the type 400. Consequently, each of the planes (400), (040) and (004) was employed in turn. Further, since the ease or otherwise of the eventual "finger printing" could not be predicted, it was decided to take four topographs using each of the three planes of {400}, thus obtaining four different views or aspects of each stone with each reflection. The final record thus comprised twelve diffraction topographs of each stone. $MoK\alpha_1$ radiation was used throughout and the procedures for taking each topograph were standard. The three rough stones were then cut and polished into the form of brilliants, which process completely changed their size and shape. X-ray diffraction topographs of the three cut brilliants were taken and no difficulty was had in matching up the topographs of a given stone in its rough and final state, thereby uniquely identifying from which rough stone each particular brilliant had been fashioned. FIGS. 3 and 4 show, by way of illustration, topographs taken of one of the diamonds before and after cutting respectively. Like numerals have been used on the drawings to illustrate common features by means of which it was possible uniquely to identify the origin of the cut and polished diamond.

The method of the invention may be used in "finger printing" other precious stones such as rubies, emeralds or sapphires.

I claim:

1. A method of determining whether a diamond to be identified is the same as or different to a known diamond including the steps of producing one or more records of internal defects of the diamond to be identified using X-ray topography and comparing the records so produced with similar records produced from the known diamond.

2. A method according to claim 1 wherein the records are those produced using X-ray diffraction at the Bragg angle.

3. A method according to claim 1 wherein the records of the specimen are produced by so orienting the specimen with respect to the range of orientations of the X-rays contained in the X-ray beam incident upon the specimen that a fraction of the volume of the specimen substantially satisfies the condition of X-ray diffraction at the Bragg angle.

4. A method according to claim 1 wherein the records of the specimen are produced by illuminating the specimen with an X-ray beam whose spectral distribution and whose range of orientations with respect to the specimen are so chosen that a fraction of the specimen departs from exact satisfaction of the condition of X-ray diffraction at the Bragg angle by a determined small angle.

5. A method according to claim 1 wherein the records are X-ray topographs.

6. A method according to claim 1 wherein the known diamond is an uncut diamond.

7. A method according to claim 1 wherein the records of a selected region of the specimen are produced by illuminating the specimen with an X-ray beam whose spectral distribution and whose range of orientations with respect to said selected region of the specimen are so chosen that a fraction of said selected region of the specimen departs from exact satisfaction of the condition of X-ray diffraction at the Bragg angle by a determined small angle.

8. A method according to claim 1 wherein said records are produced using monochromatic radiation.

9. A method according to claim 1 wherein surface damage is removed from the diamond prior to records being produced.

10. A method according to claim 9 wherein surface damage is removed by etching.

11. A method according to claim 1 wherein the known diamond is a rough diamond.

12. A method according to claim 11 wherein the diamond to be identified is a partially cut diamond.

13. A method according to claim 11 wherein the diamond to be identified is a fully cut diamond.

14. A method according to claim 1 wherein the records of a selected region of the specimen are produced by so orienting the specimen with respect to the range of orientations of the X-rays contained in the X-ray beam incident upon the specimen that a fraction of the volume of said selected region of the specimen substantially satisfies the condition of X-ray diffraction at the Bragg angle.

15. A method according to claim 14 including producing the records from the known diamond and the diamond to be identified according to a predetermined routine.

16. A method according to claim 15 wherein said predetermined routine comprises a series of diffraction radiographs using crystallographically equivalent reflections.

17. A method according to claim 15 wherein said predetermined routine comprises selecting three cube planes in each of which four radiographs are taken, the crystal being rotated 90° around a perpendicular to the plane between each radiograph.

* * * * *